US010082468B2

(12) United States Patent
Kwon

(10) Patent No.: US 10,082,468 B2
(45) Date of Patent: Sep. 25, 2018

(54) METHOD FOR EVALUATING SERS SENSOR SUBSTRATE

(71) Applicant: KOREA RESEARCH INSTITUTE OF STANDARDS AND SCIENCE, Daejeon (KR)

(72) Inventor: Hyuksang Kwon, Daejeon (KR)

(73) Assignee: KOREA RESEARCH INSTITUTE OF STANDARDS AND SCIENCE, Daejeon (KR)

(*) Notice: Subject to any disclaimer, the term of this patent is extended or adjusted under 35 U.S.C. 154(b) by 0 days.

(21) Appl. No.: 15/580,117

(22) PCT Filed: Apr. 27, 2017

(86) PCT No.: PCT/KR2017/004474
§ 371 (c)(1),
(2) Date: Dec. 6, 2017

(87) PCT Pub. No.: WO2017/188744
PCT Pub. Date: Nov. 2, 2017

(65) Prior Publication Data
US 2018/0136136 A1 May 17, 2018

(30) Foreign Application Priority Data
Apr. 27, 2016 (KR) ........................ 10-2016-0051363

(51) Int. Cl.
*G01J 3/44* (2006.01)
*G01N 21/65* (2006.01)
*G01N 21/25* (2006.01)

(52) U.S. Cl.
CPC ......... *G01N 21/658* (2013.01); *G01N 21/255* (2013.01); *G01N 2201/06113* (2013.01); *G01N 2201/12* (2013.01)

(58) Field of Classification Search
CPC ... G01J 3/02; G01J 3/44; G01N 21/65; G01N 21/658; G01N 21/255; G01N 2021/656; G01B 11/16
See application file for complete search history.

(56) References Cited

U.S. PATENT DOCUMENTS

2010/0053598 A1* 3/2010 Kwon .................... G01B 11/16
356/32

FOREIGN PATENT DOCUMENTS

| KR | 10-2011-0047921 | 5/2011 |
| KR | 10-2012-0134910 | 12/2012 |

(Continued)

OTHER PUBLICATIONS

International Search Report for corresponding International PCT Application No. PCT/KR2017/004474, dated Jul. 19, 2017.

*Primary Examiner* — Abdullahi Nur
(74) *Attorney, Agent, or Firm* — Hauptman Ham, LLP

(57) ABSTRACT

The present invention relates to a method for evaluating a SERS sensor substrate, comprising the steps of: a) measuring, through a dark-field microscope, the color of nanoparticles positioned on the SERS sensor substrate; b) converting the measured color into a distance between the nanoparticles; c) acquiring the Raman signal intensity of the SERS sensor substrate; d) acquiring the standard Raman signal intensity of a standard SERS sensor substrate including the nanoparticles having the distance that is the same as the converted distance; and e) comparing the Raman signal intensity and the standard Raman signal intensity.

9 Claims, 2 Drawing Sheets

(56) References Cited

FOREIGN PATENT DOCUMENTS

| | | |
|---|---|---|
| KR | 10-1448111 | 10/2014 |
| KR | 10-2015-0000751 | 1/2015 |
| KR | 10-2016-0038205 | 4/2016 |

* cited by examiner

METHOD FOR EVALUATING SERS SENSOR SUBSTRATE

TECHNICAL FIELD

The present invention relates to an evaluation method of a substrate for a surface enhanced Raman scattering (SERS) sensor.

BACKGROUND ART

The identification of the development of nanostructures and biosystems through various fluorescent markers has the potential to lead to the technical difficulties of labeling and the false results of fluorescent markers. Therefore, research is being conducted through the detection of Raman signal inherent to the substance without labeling.

However, there is a practical limit to the detection of Raman signal because it has a very small intensity compared to fluorescence.

To unravel the issue, the researches on SERS sensors using gold or silver nanostructure are actively underway.

This is due to the use of surface Plasmon in the metal structure confined to nanometer size, that is, Localized Surface Plasmon Resonance (LSPR). Biosensor applications such as detection of a very small amount of biomolecules by Raman signal amplification will be possible when resonance energy is irradiated for metal nanostructure. In addition, the optimal SERS sensor structure enables Raman enhancement of $10^8$ or more, enabling single molecule detection.

Various studies have been reported to maximize the SERS signal: synthesis of various types of nanoparticles [Jianping Xie, Jim Yang Lee, and Daniel I. C. Wang, 2007, Chem. Mater., 19, 2823-2830], the strong electric field between nanoparticles under LSPR [Ping-Ji Huang, et al, 2009, Adv. funct. Mater., 19, 242-248], a stimulus-responsive polymer to control the nanogap-distance between nanoparticles [Laura Rodriguez-Lorenzo, et al. 2009, J. AM. CHEM. SOC, 131, 4616-4618]. Therefore, the substrate for the SERS sensor capable of high sensitivity biosensing and chemical sensing with only a small amount of sample can be considered.

However, a method for evaluating whether or not such a substrate for an SERS sensor is well manufactured to have excellent performance is not known, and a simple and systematic method for evaluating a substrate for an SERS sensor is needed.

DISCLOSURE

Technical Problem

An object of the present invention is to provide a simple and systematic evaluation method of a substrate for an SERS sensor.

Technical Solution

In one general aspect, an evaluation method of a substrate for a surface enhanced Raman scattering (SERS) sensor includes: a) measuring colors of nanoparticles located on the substrate for the SERS sensor using a dark field microscope; b) converting the measured colors into distances between the nanoparticles; c) obtaining a Raman signal intensity of the substrate for the SERS sensor; d) obtaining a standard Raman signal intensity of a standard substrate for the SERS sensor including the nanoparticle having the same distance as the converted distance; and e) comparing the Raman signal intensity and the standard Raman signal intensity with each other.

Advantageous Effects

According to the evaluation method of the substrate for the SERS sensor according to the present invention, it is possible to evaluate the performance of the substrate for the SERS sensor and whether or not the substrate for the SERS sensor is well manufactured as planned through the simple and systematic method.

BEST MODE

Figure 1:
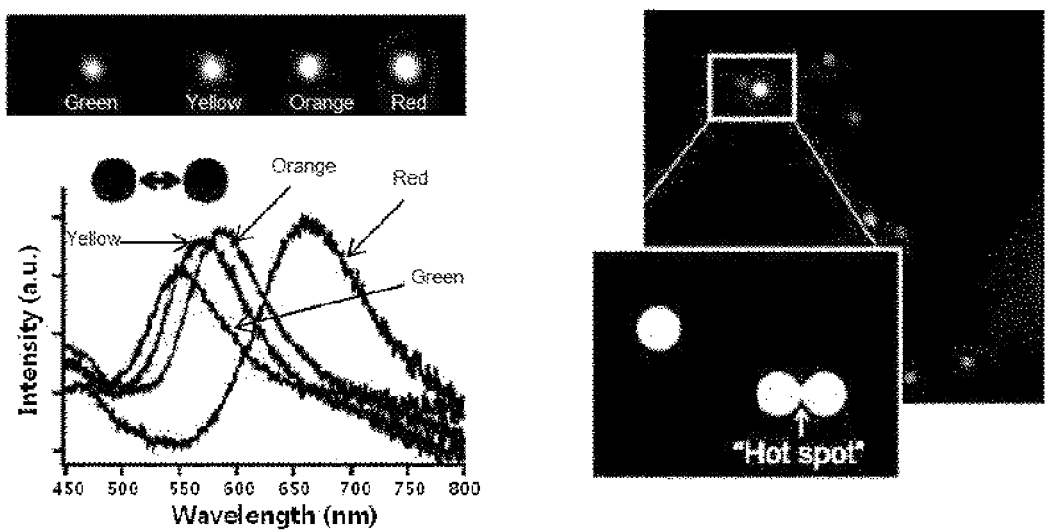
FIG. 1 shows a distance between nanoparticles according to colors on a dark field image according to an exemplary embodiment of the present invention.

The present invention relates to an evaluation method of a substrate for an SERS sensor, and more particularly, to a method capable of evaluating performance of a substrate for an SERS sensor and whether or not the substrate for the SERS sensor is well manufactured as planned, by a simple and systematic method.

Specifically, the evaluation method of the substrate for the SERS sensor may be performed by including a) measuring colors of nanoparticles located on the substrate for the SERS sensor using a dark field microscope; b) converting the measured colors into a distance between the nanoparticles; c) obtaining a Raman signal intensity of the substrate for the SERS sensor; d) obtaining a standard Raman signal intensity of a standard substrate for the SERS sensor including the nanoparticle having the same distance as the converted distance; and e) comparing the Raman signal intensity and the standard Raman signal intensity with each other. Here, the operations c) and d), which are each operations independent from each other, may be performed without particular order.

The substrate for the SERS sensor according to the present invention is manufactured by positioning a marker molecule between a nano-thin film and the nanoparticle, which is one of the typical methods, and specifically, a substrate for a 'surface enhanced Raman scattering (SERS)' may be manufactured by forming a self-assembled monolayer on the nano-thin film having a thickness of 10 to 20 nm and then dispersing the nanoparticles having a size of 50 to 100 nm thereon.

Here, a substance according to an exemplary embodiment is not particularly limited and may be used as long as it is typically used in the art, and specifically, glass, plastic, metal, silicon, quartz, alumina, or the like may be used.

The nano-thin film according to an exemplary embodiment is not particularly limited and may be used as long as it is typically used in the art, and for example, a metal nano-thin film may be used, and more specifically, the nano thin-film formed of gold, silver, copper, titanium, aluminum, platinum, or the like may be used.

The self-assembled monolayer according to an exemplary embodiment may preferably use a compound capable of being well bonded to the nano-thin film and the nanoparticles to amplify intensity of the surface enhanced Raman scattering, and may be formed by using a monomer compound having a functional group such as, for example, —NCS, —NCO, —NH$_2$, —COOH, —NO$_2$, —CN, —SH, or the like.

The nanoparticle according to an exemplary embodiment is not particularly limited and may be used as long as it is the nanoparticle capable of performing the surface enhanced Raman scattering. For example, the nanoparticle may be a metal nanoparticle, and more specifically, may be, for example, gold, silver, platinum, copper, palladium, aluminum, zinc, or a mixture thereof. The nanoparticle may have a spherical shape, a rod shape, a polyhedral shape, a plate shape, or the like, and the polyhedral shape may be a hexahedral shape, an octahedral shape, a truncated one shape, an icosahedral shape, or the like, but is not limited thereto. In addition, an average particle diameter of the nanoparticles is not particularly limited as long as a size thereof may perform the surface enhanced Raman scattering, but may be, for example, 5 to 1,000 nm and more preferably 20 to 200 nm. Here, in a case in which the average particle diameter of the nanoparticles is too small such as 5 nm or less, since it is difficult to obtain Raman signal intensity, it is not preferable.

The substrate for the SERS sensor manufactured as described above may evaluate how well the substrate for the SERS sensor is manufactured by using a simple measurement method.

A method for measuring colors using a dark-field microscope will be described in more detail. The dark-field microscope is designed to focus light to a sample at an oblique angle of an objective lens using the special objective lens so that only light scattered by the sample passes through the objective lens and appears, and light that does not pass through the sample does not enter the objective lens, and according to the present invention, only light scattered by the nanoparticles located on the substrate for the SERS sensor passes through the objective lens and shows the colors on a dark-field image and a region in which the nanoparticles are not present appears as a black background on the dark-field image.

The measurement of the colors according to an exemplary embodiment of the present invention may be the measurement of colors of a plurality of nanoparticles on the substrate for the SERS sensor. In detail, the measurement of the colors may be the measurement of colors of two nanoparticles, or the measurement of nanoparticles within a predetermined region of the substrate for the SERS sensor. Here, the predetermined region may mean a partial region or an entire region of the substrate for the SERS sensor.

As an example of the colors appearing on the dark-field image, when the two nanoparticles are located close to each other, a red shift occurs as a distance between the nanoparticles approaches, so colors having a long wavelength may appear in the order of green, yellow, orange, and red. Here, the distance between the nanoparticles may be measured by using a typical method, and specifically, the distance between the nanoparticles may be measured by a scanning electron microscope (SEM), an atomic force microscope (AFM), a transmission electron microscope (TEM), or the like, for example.

Figure 2:
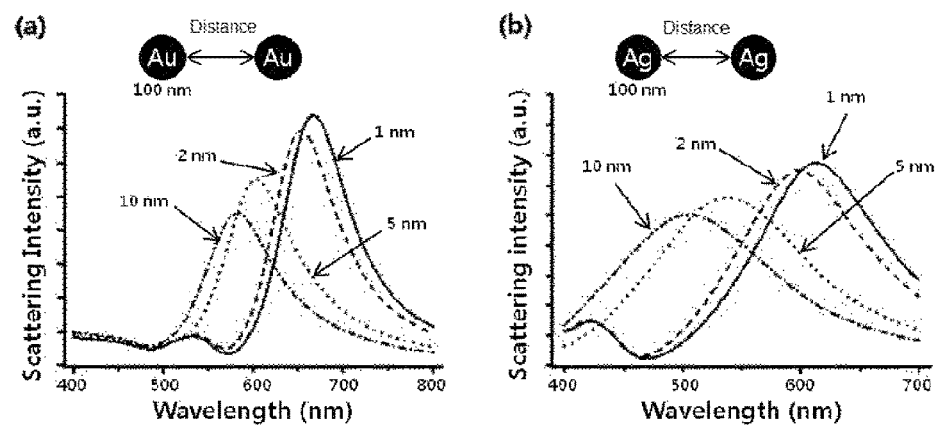
FIGS. 2A and 2B show wavelength-scattering signal intensity spectrums obtained by simulating a distance between gold nanoparticles and a distance between silver nanoparticles with a finite-difference time-domain (FDTD) method.

FIG. 2 shows a wavelength-scattering signal intensity spectrum obtained by simulating a relationship between a distance between two metal nanoparticles and color (scattered color) on the dark-field image with a finite-difference time-domain (FDTD) method, and it may be confirmed that the color on the dark-field image is varied according to the distance between the nanoparticles. Although FIG. 2 shows a simulation result, the distance between the particles may be converted according to the colors measured in the dark-field image by constituting actual data on the color according to the distance between the nanoparticles in advance, as described below.

Specifically, as shown in FIG. 2A, in the case of two spherical gold (Au) nanoparticles having a particle diameter of 100 nm, a distance between two nanoparticles in which color of a dark-field image is red ($\lambda_{max}$ 665 to 675 nm) may be 1 nm, a distance between two nanoparticles in which color thereof is red ($\lambda_{max}$ 650 to 660 nm) may be 2 nm, a distance between two nanoparticles in which color thereof is orange ($\lambda_{max}$ 600 to 610 nm) may be 5 nm, and a distance between two nanoparticles in which color thereof is yellow ($\lambda_{max}$ 575 to 585 nm) may be 10 nm.

As another example, as shown in FIG. 2B, in the case of two spherical silver (Ag) nanoparticles having a particle diameter of 100 nm, a distance between two nanoparticles in which color of the dark-field image is orange ($\lambda_{max}$ 610 to 620 nm) may be 1 nm, a distance between two nanoparticles in which color thereof is orange ($\lambda_{max}$ 595 to 605 nm) may be 2 nm, a distance between two nanoparticles in which color thereof is green ($\lambda_{max}$ 530 to 540 nm) may be 5 nm, and a distance between two nanoparticles in which color thereof is green ($\lambda_{max}$ 500 to 510 nm) may be 10 nm.

According to an exemplary embodiment of the present invention, a light source used to obtain the dark-field image is not particularly limited and may be used as long as it is white light having a wavelength region of 400 to 1000 nm, and specifically, a tungsten lamp, a tungsten-halogen lamp, a xenon (Xe) lamp, or the like may be used.

When the measurement of the color is completed, the measured color may be converted into the distance between the nanoparticles. However, before performing the present operation, a database in which the distances between the particles according to the colors are standardized should be constituted in advance, and the database has to have precision and reliability. Since the color that actually appears on the dark-field image, that is, the scattered color may be varied according to variables such as the type, size, and shape of the nanoparticle, and the distance between the particles, it is necessary to obtain a database for as many cases as possible by making only one variable different and fixing the remaining variables to be equal. In a case in which the database is constituted, the substrate for the SERS sensor including nanoparticles having planned types, sizes, and shapes is manufactured, the colors of the substrate for the SERS sensor are measured by using the dark-field microscope, and the distance between the particles may be then converted according to the measured colors.

Accordingly, information on the distance between the nanoparticles may be quantitatively obtained through the colors appearing on the dark-field image, and a distribution of the distance between the nanoparticles, or the like may be confirmed based on the above-mentioned information. Such information may be effectively used in evaluating performance and a manufactured state of the substrate for the SERS sensor.

The conversion into the distance between the particles according to an exemplary embodiment of the present invention may refer to measuring the color at a single location and converting the measured color into a distance, or measuring colors at a plurality of locations, converting the measured colors into distances, and then averaging the converted distances.

As described above in the color measurement, the colors may be measured for the plurality of nanoparticles on the substrate for the SERS sensor, and specifically, may be the measurement of the colors of the two nanoparticles, or the measurement of the nanoparticles within the predetermined region of the substrate for the SERS sensor Here, the predetermined region may mean a partial region or an entire region of the substrate for the SERS sensor.

Accordingly, the colors measured for the two nanoparticles may be converted into the distance between the two nanoparticles, or alternatively, the colors measured in the predetermined region of the substrate for the SERS sensor are each converted into the distances and the converted distances are then averaged, thereby making it possible to calculate an average distance. As described above, the predetermined region may mean the partial region or the entire region of the substrate for the SERS sensor.

Next, Raman signal intensity of the substrate for the SERS sensor and standard Raman signal intensity of the substrate for the SERS sensor may be obtained. As described above, the two operations, which are each performed independently from each other, may be performed without particular order.

The Raman signal intensity may be obtained by using a typical method, and particularly, may be measured by irradiating laser on the manufactured substrate for the SERS sensor. The laser for obtaining the Raman signal intensity may be used without being particularly limited as long as it is commonly used for Raman spectroscopic measurement, but it is preferable to irradiate laser light energy that is equivalent to plasmon resonance energy of a Raman sensor. Specifically, argon ion laser, helium-neon laser, diode laser, or the like may be used, but the laser is not limited thereto.

Here, the Raman signal intensity may be obtained at a signal location at which the color is measured or obtained on an entire surface of the substrate for the SERS sensor. In particular, in a case in which the Raman signal intensity is obtained on the entire surface of the substrate for the SERS sensor, it is more effective in evaluating the performance of the substrate for the SERS sensor or whether or not the substrate for the SERS sensor is well manufactured.

The standard Raman signal intensity may be measured by actually manufacturing a standard substrate for an SERS sensor to irradiate laser thereto, or using a simulation tool calculated based on a quantum mechanical theory.

Here, the standard substrate for the SERS sensor refers to the substrate for the SERS sensor characterized in that variables such as the type, size, and shape of the nanoparticle and the distance between the particles have high reliability, and the standard substrate for the SESR sensor may be a standard model of the substrate for the SERS sensor designed according to the present invention.

In a case in which it is intended to obtain the standard Raman signal intensity by irradiating the laser to the standard substrate for the SERS sensor, the standard Raman signal intensity may be obtained by using the same method as the method for obtaining the Raman signal intensity.

Next, the substrate for the SERS sensor may be evaluated by comparing the Raman signal intensity and the standard Raman signal intensity which are each obtained with each other.

For example, in a case in which the Raman signal intensity coincides with the standard Raman signal intensity at 90% or more, it may be evaluated that the Raman sensor is well manufactured as planned, and in a case in which the Raman signal intensity coincides with the standard Raman signal intensity at 98% or more, it may be evaluated that the Raman sensor is very precisely manufactured with high reliability. On the other hand, in a case in which the Raman signal intensity coincides with the standard Raman signal intensity at less than 90%, it may be evaluated that the Raman sensor is not manufactured as planned.

Further, the manufactured state and the performance of the substrate for the SERS sensor may be more efficiently evaluated based on the information such as the distribution of the distances between the nanoparticles obtained from the dark-field image, in addition to the comparison between the Raman signal intensity and the standard Raman signal intensity a described above.

Meanwhile, such a difference may occur by various reasons, and for example, unlikely as being planned, the shape of the particle may be varied or an arrangement structure between the particles may be varied due to agglomeration of the nanoparticles.

Unless defined otherwise in the present invention, all technical terms and scientific terms have the same meaning as the meaning which is generally understood by one of ordinary skill in the art to which the present invention belongs. The terms used herein are merely for the purpose of effectively describing the particular exemplary embodiments and are not intended to limit the present invention.

The drawings of the present invention to be described below are provided by way of example so that the idea of the present invention can be sufficiently transferred to those skilled in the art. Therefore, the present invention is not be limited to the drawings presented below but may be implemented in different forms, and the drawings presented below will be exaggerated to clearly understand the spirit of the present invention.

In addition, the singular forms used in the specification and the appended claims are intended to include the plural forms as well, unless the context clearly indicates otherwise.

The invention claimed is:

1. An evaluation method of a substrate for a surface enhanced Raman scattering (SERS) sensor, the evaluation method comprising:
   a) measuring colors of nanoparticles located on the substrate for the SERS sensor using a dark field microscope;
   b) converting the measured colors into distances between the nanoparticles;
   c) obtaining a Raman signal intensity of the substrate for the SERS sensor;
   d) obtaining a standard Raman signal intensity of a standard substrate for the SERS sensor including the nanoparticle having the same distance as the converted distance; and
   e) comparing the Raman signal intensity and the standard Raman signal intensity with each other.

2. The evaluation method of claim 1, wherein the nanoparticle is a metal nanoparticle.

3. The evaluation method of claim 2, wherein the metal nanoparticle is gold, silver, platinum, copper, palladium, aluminum, zinc, or a mixture thereof.

4. The evaluation method of claim 1, wherein an average particle diameter of the nanoparticles is 5 to 1,000 nm.

5. The evaluation method of claim 1, wherein the Raman signal intensity in step c) is obtained by irradiating laser.

6. The evaluation method of claim 5, wherein the laser is argon ion laser, helium-neon laser or diode laser.

7. The evaluation method of claim 1, wherein the Raman signal intensity in step c) is obtained at a single location at which the color is measured.

8. The evaluation method of claim 1, wherein the Raman signal intensity in step c) is obtained on an entire surface of the substrate for the SERS sensor.

9. The evaluation method of claim 1, wherein in step b), the colors are measured at a plurality of locations, the measured colors are converted into the distances between the nanoparticles, and the converted distances are then averaged.

* * * * *